US012778935B2

(12) United States Patent
Liu

(10) Patent No.: US 12,778,935 B2
(45) Date of Patent: Nov. 3, 2026

(54) COMPOSITIONS OF BERBERINE URSODEOXYCHOLATE AND METHODS THEREOF FOR TREATING FATTY LIVER DISEASE, DIABETES AND HYPERLIPIDEMIA

(71) Applicant: SHENZHEN HIGHTIDE BIOPHARMACEUTICAL LTD., Shenzhen (CN)

(72) Inventor: Liping Liu, Shenzhen (CN)

(73) Assignee: SHENZHEN HIGHTIDE BIOPHARMACEUTICAL, LTD., Shenzhen (CN)

( * ) Notice: Subject to any disclaimer, the term of this patent is extended or adjusted under 35 U.S.C. 154(b) by 918 days.

(21) Appl. No.: 17/966,782

(22) Filed: Oct. 15, 2022

(65) Prior Publication Data

US 2023/0112845 A1 Apr. 13, 2023

Related U.S. Application Data

(63) Continuation-in-part of application No. PCT/CN2021/125490, filed on Oct. 22, 2021.

(60) Provisional application No. 63/256,141, filed on Oct. 15, 2021, provisional application No. 63/104,754, filed on Oct. 23, 2020.

(51) Int. Cl.

| | |
|---|---|
| ***A61K 31/4375*** | (2006.01) |
| ***A61K 31/191*** | (2006.01) |
| ***A61P 3/06*** | (2006.01) |
| ***A61P 3/10*** | (2006.01) |

(52) U.S. Cl.

CPC ........ *A61K 31/4375* (2013.01); *A61K 31/191* (2013.01); *A61P 3/06* (2018.01); *A61P 3/10* (2018.01); *A61K 2300/00* (2013.01)

(58) Field of Classification Search

CPC .............................. A61P 3/06; A61K 31/4375

See application file for complete search history.

(56) References Cited

FOREIGN PATENT DOCUMENTS

| | | | | |
|---|---|---|---|---|
| WO | 2016015634 A1 | | 2/2016 | |
| WO | 2018205987 A1 | | 11/2018 | |
| WO | WO2018/205987 | * | 11/2018 | ........... C07D 455/03 |

OTHER PUBLICATIONS

Di Bisceglie' et al., J'nal of Hepatology (2020) 73(supp.)1, pp. S440-S441.*

International Search Report and Written Opinion, PCT/CN/2021/125490, (Jan. 26, 2022).

Adrian Di Bisceglie, et al. "A randomized, double blind, placebo-controlled trial of htd1801 (berberine ursodeoxycholate, budc) in patients with hypercholesterolemia: implications for its use in non-alcoholic steatohepatitis (NASH)" J. of Hepatology, vol. 73, No. Supp 1, (Aug. 31, 2020).

"A Proof-of-Concept and Dose-Ranging Study Investigating the Efficacy and Safety of HTD1801 in Adults with Nonalcoholic Steatohepatitis (NASH) and Type 2 Diabetes Mellitus (T2DM)" https://cdn.clinicaltrials.gov/large-docs/44/NCT03656744/Prot_000.pdf, (Mar Mar. 27, 2019).

"A Study of HTD1801 in Adults With Nonalcoholic Steatohepatitis (NASH) and Type 2 Diabetes Mellitus (T2DM)" https://clinicaltrials.gov/study/NCT03656744?tab=history&a=26&b=26#StudyPageTop. (Jul. 23, 2020).

Stephen A. Harrison, et al. "A phase 2, proof of concept, randomised controlled trial of berberine ursodeoxycholate in patients with presumed non-alcoholic steatohepatitis and type 2 diabetes" Nature Communications vol. 12, Article No. 5503 (2021).

Adrian Di Bisceglie, et al. "Pharmacokinetics and pharmacodynamics of HTD1801 (berberine ursodeoxycholate, BUDCA) in patients with hyperlipidemia" Lipids in Health and Disease vol. 19, No. 1, 239 (Nov. 12, 2020).

* cited by examiner

*Primary Examiner* — Paul V Ward

(74) *Attorney, Agent, or Firm* — Milstein Zhang & Wu LLC

(57) ABSTRACT

The invention provides pharmaceutical compositions of berberine ursodeoxycholate (BUDCA) and methods of use thereof for the treatment fatty liver disease, diabetes, hyperlipidemia, and liver fibrosis, and related diseases and conditions.

17 Claims, 8 Drawing Sheets

COMPOSITIONS OF BERBERINE URSODEOXYCHOLATE AND METHODS THEREOF FOR TREATING FATTY LIVER DISEASE, DIABETES AND HYPERLIPIDEMIA

PRIORITY CLAIMS AND RELATED PATENT APPLICATIONS

This application is a continuation-in-part of and claims the benefit of priority to PCT/CN2021/125490, filed Oct. 22, 2021, which claims the benefit of priority to U.S. Provisional Application Ser. No. 63/104,754, filed Oct. 23, 2020. This application also claims the benefit of priority to U.S. Provisional Application Ser. No. 63/256,141, filed Oct. 15, 2021. The entire content of each of the mentioned prior applications is incorporated herein by reference.

TECHNICAL FIELD OF THE INVENTION

The invention generally relates to compositions of berberine ursodeoxycholate (BUDCA), and methods for therapeutic uses thereof. In particular, the invention relates to pharmaceutical compositions and methods of use of BUDCA for the treatment of fatty liver disease, diabetes, hyperlipidemia, and liver fibrosis, and related diseases and conditions, as monotherapy, in combination therapy with other agents or an adjuvant.

BACKGROUND OF THE INVENTION

BUDCA is a new molecular entity and can be administered orally. The compound was disclosed in WO 2016/015634 A1 (PCT/CN2015/085350) and WO 2018/205987 A1 (PCT/CN2018/086461), the content of each of which is incorporated herein by reference in its entirety. BUDCA is an ionic salt of berberine (BBR) and ursodeoxycholic acid (UDCA), represented by

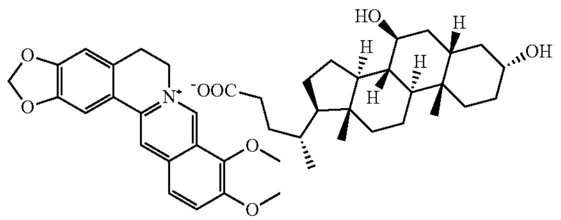

Berberine ursodeoxycholate (BUDCA)

Fatty liver disease, a.k.a. hepatic steatosis, is a condition where excess fat builds up in the liver. Fatty liver can be a reversible condition wherein large vacuoles of triglyceride fat accumulate in liver cells via the process of steatosis. Complications may include cirrhosis, liver cancer, and esophageal varices.

Non-alcoholic fatty liver disease (NAFLD) is a form of fatty liver disease that occurs when excessive fat is deposited in the liver of patients without excessive alcohol intake. NAFLD is generally recognized to be associated with metabolic syndrome such as insulin resistance, hypertension and obesity. NAFLD affects about a third of the adult population in developed countries.

Non-alcoholic steatohepatitis (NASH) is a necroinflammatory disease of the liver which may lead to fibrosis (scarring) and possible progression to cirrhosis. NASH thus is a more extreme form of NAFLD with chronic inflammation that can lead to progressive fibrosis, cirrhosis, and eventual liver failure and death. NASH is often associated with obesity, diabetes, hypertension and hyperlipidemia. A major feature of NASH is fat in the liver, along with inflammation and damage. Most people with NASH, an often "silent" liver disease, feel well and are not aware that they have a liver problem. Nevertheless, NASH can be severe and can lead to cirrhosis, when the liver is permanently damaged and scarred and no longer work properly.

Dyslipidemia is a disorder characterized by an abnormal amount of lipids (e.g., triglycerides, cholesterol and/or fat phospholipids) in the blood, including lipoprotein overproduction (hyperlipidemia) or deficiency. Dyslipidemias may be manifested by elevation of the total cholesterol, the "bad" low-density lipoprotein (LDL) cholesterol and the triglyceride concentrations, and a decrease in the "good" high-density lipoprotein (HDL) cholesterol concentration in the blood.

Hyperlipidemia is elevation of plasma cholesterol (hypercholesterolemia), triglycerides (hypertriglyceridemia), or both, or a low high-density lipoprotein level that contributes to the development of atherosclerosis. In developed countries, most dyslipidemias are hyperlipidemias. This is often due to diet and lifestyle.

Diabetes mellitus, a.k.a. diabetes, is a group of disorders characterized by high blood sugar (glucose) levels because the body does not produce enough or respond normally to insulin. It has become pandemic with an estimate of over 300 million people worldwide living with diabetes today. Without effective prevention, this number will grow up to 500 million by 2030. Diabetes can cause a wide range of health complications. Acute complications include diabetic ketoacidosis, hyperosmolar hyperglycemic state, or death. Diabetes is a common cause of dyslipidemia.

There are three main types of diabetes: type 1 diabetes, type 2 diabetes, and gestational diabetes. Among them, type 2 diabetes is the most common form of diabetes accounting for 90-95% of cases. Type 2 diabetes is characterized by impaired insulin secretion, increased hepatic glucose production, and decreased response of peripheral tissues to insulin, i.e., insulin resistance. Many therapeutic treatments are available for the management of type 2 diabetes, but they are often accompanied by various side effects. An optimal therapy should be safe and include early initiation of combination drugs with complimentary mechanisms of action.

Despite continued efforts and meaningful progress over the past decades in the understanding and management of fatty liver, diabetes, and dyslipidemia (in particular hyperlipidemia) diseases, patients with these conditions continue to have an increased risk of, and many do suffer from, a number of serious complications. Liver cancer remains a significant risk to patients with fatty liver, in particular NASH.

There are significant unmet needs for therapeutics that can be used effectively for the treatment and management of these diseases and related complications.

SUMMARY OF THE INVENTION

The invention is based in part on novel compositions and methods of use of BUDCA for treating fatty liver disease, diabetes, hyperlipidemia, and liver fibrosis, optionally as adjunctive to other agents, such as ezetimibe or bempedoic acid, or co-administered with metformin, insulin and a glucagon-likepeptide-1 (GLP-1) agonist.

In one aspect, the invention generally relates to a method for treating hyperlipidemia. The method comprises administering to a subject in need thereof a therapeutically effective amount of a pharmaceutical composition comprising BUDCA.

In another aspect, the invention generally relates to a method for reducing low density lipoprotein cholesterol (LDL-c), total cholesterol (TC), and/or triglyceride (TG). The method comprises administering to a subject in need thereof a therapeutically effective amount of a pharmaceutical composition comprising BUDCA.

In yet another aspect, the invention generally relates to a method for treating fatty liver and diabetes. The method comprises administering to a subject suffering from both fatty liver and diabetic diseases a therapeutically effective amount of a pharmaceutical composition comprising BUDCA.

In yet another aspect, the invention generally relates to a method for reducing or slowing the progression of liver fibrosis associated with fatty liver and diabetic diseases. The method comprises administering to a subject suffering from both fatty liver and diabetic diseases a therapeutically effective amount of a pharmaceutical composition comprising BUDCA.

In yet another aspect, the invention generally relates to a unit dosage form comprising from about 250 mg to about 2,500 mg (e.g., about 500 mg to about 2,000 mg, about 500 mg to about 1,500 mg, about 1,000 mg to about 2,500 mg, about 500 mg to about 1,000 mg) of BUDCA.

In yet another aspect, the invention generally relates to use of BUDCA for treating fatty liver and diabetic diseases.

In yet another aspect, the invention generally relates to use of BUDCA for treating NASH and type 2 diabetes.

In yet another aspect, the invention generally relates to use of BUDCA for treating hyperlipidemia.

In yet another aspect, the invention generally relates to use of BUDCA for reducing LDL-c, TC and/or TG.

DEFINITIONS

Figure 1:
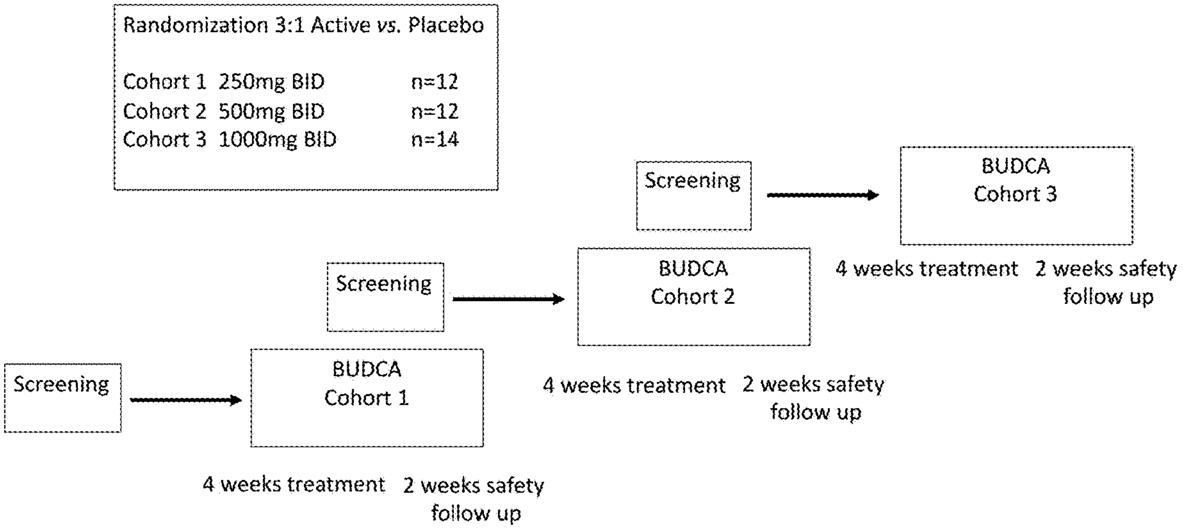
FIG. 1 depicts the phase 1b study overview and randomization scheme.

Unless defined otherwise, all technical and scientific terms used herein have the same meaning as commonly understood by one of ordinary skill in the art to which this invention belongs. General principles of organic chemistry, as well as specific functional moieties and reactivity, are described in “Organic Chemistry”, Thomas Sorrell, University Science Books, Sausalito: 2006.

As used herein, the term “effective amount” of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term “treating”, “reducing”, or “preventing” “a disease or disorder” refers to ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

As used herein, the term “pharmaceutically acceptable excipient, carrier, or diluent” refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be “acceptable” in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer’s solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the terms “isolated” or “purified” refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the term “subject” refers to any animal (e.g., a mammal), including, but not limited to humans, non-human primates, rodents, and the like, which is to be the recipient of a particular treatment. Typically, the terms “subject” and “patient” are used interchangeably herein in reference to a human subject.

Compounds of the present invention are, subsequent to their preparation, preferably isolated and purified to obtain a composition containing an amount by weight equal to or greater than 95% (“substantially pure”), which is then used or formulated as described herein. In certain embodiments, the compounds of the present invention are more than 99% pure.

DETAILED DESCRIPTION OF THE INVENTION

The present invention is based in part on data obtained from phase 1b and phase 2 randomized, placebo-controlled clinical trials where BUDCA was orally administered and well tolerated. The trial results showed that BUDCA was very effective in decreasing liver fat content (LFC, as assessed by MRI-PDFF) and liver fibrosis markers such as AST to Platelet Ratio Index (APRI) and Fibrosis-4 (FIB-4) in patients with presumed NASH and diabetes. BUDCA was also effective in improving glycemic control, measured by reductions in blood levels of HbA1c. In addition to these key benefits, improvements were seen in levels of liver-associated enzymes (ALT and GGT) as well as lipid levels (LDL-c and TG). Furthermore, BUDCA has a significant albeit modest effect in safely lowering serum LDL-c concentrations in individuals with a history of hypercholesterolemia.

The present invention provides novel compositions and methods of use of BUDCA for treating fatty liver disease, diabetes, hyperlipidemia, and liver fibrosis, as primary treatment or as adjunctive to other agents, such as ezetimibe or bempedoic acid, or co-administered with metformin, insulin and a GLP-1 agonist.

In one aspect, the invention generally relates to a method for treating hyperlipidemia. The method comprises administering to a subject in need thereof a therapeutically effective amount of a pharmaceutical composition comprising BUDCA.

In certain embodiments, the subject additionally suffers from diabetes and the method comprises treating hyperlipidemia and diabetes.

In certain embodiments, the subject suffers from hypercholesterolemia.

In another aspect, the invention generally relates to a method for reducing LDL-c, TC, and/or TG. The method comprises administering to a subject in need thereof a therapeutically effective amount of a pharmaceutical composition comprising BUDCA.

In certain embodiments for treating hyperlipidemia and/or reducing LDL-c, the subject is administered from about 250 mg/day to about 5,000 mg/day (e.g., about 250 mg/day to about 4,000 mg/day, about 1,000 mg/day to about 2,500 mg/day, about 500 mg/day to about 2,000 mg/day, about 500 mg/day to about 1,500 mg/day, about 500 mg/day to about 1,000 mg/day, about 1,000 mg/day to about 2,500 mg/day, about 1,500 mg/day to about 2,500 mg/day, about 2,000 mg/day to about 5,000 mg/day) of BUDCA.

In certain embodiments for treating hyperlipidemia and/or reducing LDL-c, the subject is administered from about 500 mg/day to about 2,500 mg/day (e.g., about 500 mg/day to about 2,000 mg/day, about 500 mg/day to about 1,500 mg/day, about 500 mg/day to about 1,000 mg/day, about 750 mg/day to about 2,000 mg/day, about 1,000 mg/day to about 2,000 mg/day) of BUDCA In certain embodiments for treating hyperlipidemia and/or reducing LDL-c, the subject is administered from about 500 mg to about 1,500 mg (e.g., about 500 mg to about 1,250 mg, about 500 mg to about 1,000 mg, about 750 mg to about 1,500 mg) BID of BUDCA.

In certain embodiments for treating hyperlipidemia and/or reducing LDL-c, administration of BUDCA lasts at least 9 weeks (e.g., at least 12 weeks, at least 15 weeks, at least 18 weeks, at least 24 weeks, or at least 36 weeks).

In certain embodiments for treating hyperlipidemia and/or reducing LDL-c, TC and/or TG, BUDCA is in the form of Form A.

In certain embodiments for treating hyperlipidemia and/or reducing LDL-c, TC and/or TG, BUDCA is a hydrate.

In certain embodiments for treating hyperlipidemia and/or reducing LDL-c, TC and/or TG, BUDCA is a hemi-nonahydrate.

In certain embodiments for treating hyperlipidemia and/or reducing LDL-c, TC and/or TG, the subject is also administered one or more of metformin, insulin and a GLP-1 agonist.

In yet another aspect, the invention generally relates to a method for treating fatty liver and diabetes. The method comprises administering to a subject suffering from both fatty liver and diabetic diseases a therapeutically effective amount of a pharmaceutical composition comprising BUDCA.

In certain embodiments, the fatty liver disease is NASH and the diabetic disease is type 2 diabetes. In certain embodiments, the subject additionally suffers from hyperlipidemia.

In certain embodiments for treating fatty liver and diabetes, the subject is administered about 250 mg/day to about 5,000 mg/day (e.g., about 250 mg/day to about 4,000 mg/day, about 1,000 mg/day to about 2,500 mg/day, about 500 mg/day to about 2,000 mg/day, about 500 mg/day to about 1,500 mg/day, about 500 mg/day to about 1,000 mg/day, about 1,000 mg/day to about 2,500 mg/day, about 1,500 mg/day to about 2,500 mg/day, about 2,000 mg/day to about 5,000 mg/day) of BUDCA.

In certain embodiments for treating fatty liver and diabetes, the subject is administered from about 500 mg/day to about 2,500 mg/day (e.g., about 500 mg/day to about 2,000 mg/day, about 500 mg/day to about 1,500 mg/day, about 500 mg/day to about 1,000 mg/day, about 750 mg/day to about 2,000 mg/day, about 1,000 mg/day to about 2,000 mg/day) of BUDCA.

In certain embodiments for treating fatty liver and diabetes, the subject is administered from about 500 mg to about 1,500 mg (e.g., about 500 mg to about 1,250 mg, about 500 mg to about 1,000 mg, about 750 mg to about 1,500 mg) BID of BUDCA.

In certain embodiments for treating fatty liver and diabetes, administration of BUDCA lasts at least 9 weeks (e.g., at least 12 weeks, at least 15 weeks, at least 18 weeks, at least 24 weeks, or at least 36 weeks).

In certain embodiments for treating hyperlipidemia and/or reducing LDL cholesterol, BUDCA is in the form of Form A.

In certain embodiments for treating fatty liver and diabetes, BUDCA is a hydrate.

In certain embodiments for treating fatty liver and diabetes, BUDCA is a hemi-nonahydrate.

In certain embodiments for treating fatty liver and diabetes, the subject additionally suffers from hyperlipidemia.

In certain embodiments for treating fatty liver and diabetes, the subject is also administered one or more of metformin, insulin and a GLP-1 agonist (e.g., exenatide, liraglutide).

In certain embodiments, the method of the invention relates to treating a subject that is unable to take or tolerate statin.

In yet another aspect, the invention generally relates to a method for reducing or slowing the progression of liver fibrosis associated with fatty liver and diabetic diseases. The method comprises administering to a subject suffering from both fatty liver and diabetic diseases a therapeutically effective amount of a pharmaceutical composition comprising BUDCA.

In certain embodiments, the fatty liver disease is NASH and the diabetic disease is type 2 diabetes. In certain embodiments, the subject additionally suffers from hyperlipidemia.

In certain embodiments, at least one of APRI and FIB-4 of the subject is reduced by at least about three-fold.

In certain embodiments, both APRI and FIB-4 of the subject are reduced. By at least about three-fold.

In certain embodiments, administration of BUDCA also simultaneously reduces at least one of low-density lipoprotein cholesterol (LDL-c), total cholesterol (TC), triglyceride (TG), alanine aminotransferase (ALT), GGT, liver fact content (LFC), and body weight.

In certain embodiments, administration of BUDCA also simultaneously reduces all of low-density lipoprotein cholesterol (LDL-c), total cholesterol (TC), triglyceride (TG), alanine aminotransferase (ALT), GGT, liver fact content (LFC), and body weight.

In certain embodiments, the subject simultaneously exhibits liver functional or histologic improvement.

In certain embodiments for reducing or slowing the progression of liver fibrosis, the subject is administered about 250 mg/day to about 5,000 mg/day (e.g., about 250 mg/day to about 4,000 mg/day, about 1,000 mg/day to about 2,500 mg/day, about 500 mg/day to about 2,000 mg/day, about 500 mg/day to about 1,500 mg/day, about 500 mg/day to about 1,000 mg/day, about 1,000 mg/day to about 2,500 mg/day, about 1,500 mg/day to about 2,500 mg/day, about 2,000 mg/day to about 5,000 mg/day) of BUDCA.

In certain embodiments for reducing or slowing the progression of liver fibrosis, the subject is administered from about 500 mg/day to about 2,500 mg/day (e.g., about 500 mg/day to about 2,000 mg/day, about 500 mg/day to about 1,500 mg/day, about 500 mg/day to about 1,000 mg/day, about 750 mg/day to about 2,000 mg/day, about 1,000 mg/day to about 2,000 mg/day) of BUDCA.

In certain embodiments for reducing or slowing the progression of liver fibrosis, the subject is administered from about 500 mg to about 1,500 mg (e.g., about 500 mg to about 1,250 mg, about 500 mg to about 1,000 mg, about 750 mg to about 1,500 mg) BID of BUDCA.

In certain embodiments for reducing or slowing the progression of liver fibrosis, administration of BUDCA lasts at least 9 weeks (e.g., at least 12 weeks, at least 15 weeks, at least 18 weeks, at least 24 weeks, or at least 36 weeks).

In certain embodiments for treating hyperlipidemia and/or reducing LDL cholesterol, BUDCA is in the form of Form A.

In methods of treatment disclosed herein, a treatment may result in a body weight loss in the subject of at least 2.0 kg (e.g., at least 2.5 kg, at least 3.0 kg, or at least 3.5 kg).

In certain embodiments for treating fatty liver and diabetes, BUDCA is a hydrate.

In certain embodiments for treating fatty liver and diabetes, BUDCA is a hemi-nonahydrate.

In yet another aspect, the invention generally relates to a unit dosage form comprising from about 250 mg to about 2,500 mg (e.g., about 500 mg to about 2,000 mg, about 500 mg to about 1,500 mg, about 1,000 mg to about 2,500 mg, about 500 mg to about 1,000 mg) of BUDCA.

In certain embodiments of the unit dosage form, BUDCA is in the form of Form A.

In certain embodiments of the unit dosage form, BUDCA is a hydrate.

In certain embodiments of the unit dosage form, BUDCA is a hemi-nonahydrate.

In certain embodiments, the unit dosage form is in the form of a capsule.

In certain embodiments, the unit dosage form is in the form of a tablet.

In certain embodiments, the unit dosage form comprises BUDCA and one or more pharmaceutically acceptable excipients, carriers, or diluents.

In yet another aspect, the invention generally relates to use of BUDCA for treating fatty liver and diabetic diseases.

In yet another aspect, the invention generally relates to use of BUDCA for treating NASH and type 2 diabetes.

In yet another aspect, the invention generally relates to use of BUDCA for treating hyperlipidemia.

In yet another aspect, the invention generally relates to use of BUDCA for reducing LDL-c, TC and/or TG.

Various solid and crystalline forms of BUDCA may be employed in the invention disclosed herein.

In certain embodiments, Form A of BUDCA, having an X-ray powder diffraction (XRPD) pattern comprising one or more peaks at 2θθ values selected from the group consisting of: 3.98, 7.06, 7.34, 7.93, 8.79, 9.47, 11.70, 11.94, 12.34, 12.55, 13.90, 14.17, 15.14, 15.50, 16.16, 16.54, 16.78, 17.53, 17.67, 18.23, 19.03, 19.98, 20.87, 21.13, 21.96, 23.49, 24.24, 24.97, 25.50, 26.63, 27.60, 28.06, 28.63, 29.40 and 30.49° (±0.2°) obtained using Cu Kα radiation ($\lambda_1$=1.540598 Å, $\lambda_2$=1.544426 Å, intensity ratio $\lambda_2/\lambda_1$=0.50), is employed.

In certain embodiments, Form B of BUDCA, having an X-ray powder diffraction (XRPD) pattern comprising one or more peaks at 2θ values selected from the group consisting of: 7.39, 9.31, 12.41, 13.14, 14.37, 14.76, 15.53, 18.65, 21.79, 22.87, 25.27, 25.53 and 28.12° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, Form C of BUDCA, having an X-ray powder diffraction (XRPD) pattern comprising one or more peaks at 2θ values selected from the group consisting of: 7.23, 10.42, 12.10, 13.37, 14.24, 14.48, 15.28, 15.95, 17.00, 18.17, 20.12, 21.77 and 25.47° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, Form D of BUDCA, having an X-ray powder diffraction (XRPD) pattern comprising one or more peaks at 2θ values selected from the group consisting of: 4.24, 6.79, 8.50, 10.25, 11.50, 13.62, 14.74, 15.20, 17.92, 18.39, 22.91 and 25.73° (±0.2°) obtained using Cu Kα radiation (($\lambda_1$=1.540598 Å, $\lambda_2$=1.544426 Å, intensity ratio $\lambda_2/\lambda_1$=0.50, is employed.

In certain embodiments, Form E of BUDCA, having an X-ray powder diffraction (XRPD) pattern comprising one or more peaks at 2θ values selected from the group consisting of: 8.59, 10.55, 11.36, 11.86, 12.46, 13.08, 13.38, 14.34, 15.57, 17.24, 17.72, 18.43, 19.66, 19.84, 20.35, 20.91, 21.36, 21.95, 23.21, 24.67, 25.04, 25.82, 26.12, 27.01, 27.84, 28.97, 30.35, 33.33, 34.54 and 36.06° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, Form H of BUDCA, having an X-ray powder diffraction (XRPD) pattern comprising one or more peaks at 2θ values selected from the group consisting of: 13.05, 14.63 and 25.46° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, Form I of BUDCA, having an X-ray powder diffraction (XRPD) pattern comprising one or more peaks at 2θ values selected from the group consisting of: 4.19, 7.64, 10.03, 13.32, 13.84, 14.83, 16.73, 22.73, 25.61 and 28.57° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, Form J of BUDCA, having an X-ray powder diffraction (XRPD) pattern comprising one or more peaks at 20 values selected from the group consisting of: 4.61, 6.32, 7.38, 8.22, 9.21, 10.57, 11.73, 12.13, 12.62, 12.96, 13.87, 14.55, 14.78, 15.81, 16.48, 17.69, 18.39, 19.01, 20.06, 21.25, 22.13, 23.20, 24.47, 24.89, 26.31, 27.98, 30.25 and 33.35° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, Form P of BUDCA, having an X-ray powder diffraction (XRPD) pattern comprising one or more peaks at 2θ values selected from the group consisting of: 3.11, 5.01, 5.78, 7.26, 9.20, 10.10, 10.79, 11.65, 13.70, 14.59, 15.22, 16.19, 16.54, 17.05, 18.06, 18.68, 20.52, 21.09, 21.73, 22.49, 24.73, 25.42, 25.94 and 30.11° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, Form W of BUDCA, having an X-ray powder diffraction (XRPD) pattern comprising one or more peaks at 2θ values selected from the group consisting of: 6.49, 7.16, 8.51, 10.21, 12.01, 13.13, 13.90, 14.42, 15.18, 15.57, 16.03, 16.45, 16.74, 17.08, 17.85, 18.39, 19.61, 20.43, 21.39, 21.70, 23.51 and 25.21° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, Form X of BUDCA, having an X-ray powder diffraction (XRPD) pattern comprising one or more peaks at 2θ values selected from the group consisting of: 3.63, 6.61, 7.24, 10.49, 11.95, 13.51, 14.26, 14.54, 15.14, 16.01, 16.82, 18.28, 20.26, 21.08, 21.49, 21.90, 25.60, 26.40, 27.31, 29.34, 30.59, 31.01, 34.04, 34.68 and 36.91° (±0.2°) obtained using Cu Kα radiation ($\lambda_1$=1.540598 Å, $\lambda_2$=1.544426 Å, intensity ratio $\lambda_2/\lambda_1$=0.50, is employed.

In certain embodiments, the solid or crystalline form (e.g., Form A of BUDCA) is a hydrate of BUDCA. In certain embodiments, the solid or crystalline form (e.g., Form A of BUDCA) is a hemi-nonahydrate of BUDCA.

Figure 5:
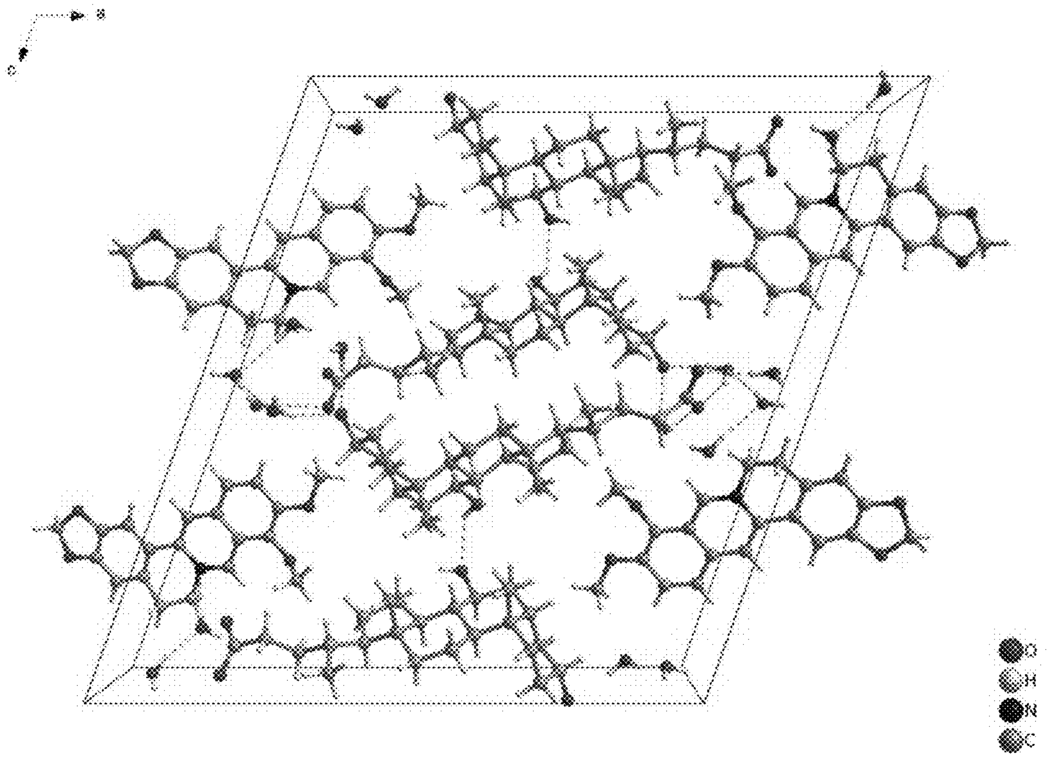
FIG. 5 depicts a unit cell of single crystalline Form A of BUDCA.

In certain embodiments, the solid or crystalline form (e.g., Form A of BUDCA) is crystalline. In certain embodiments, the crystalline form is characterized in a monoclinic crystal system and $P2_1$ space group. In certain embodiments of the crystalline form, each unit cell contains two asymmetric units and there are two BBR cations, two UDCA anions and nine $H_2O$ molecules per asymmetric unit, and four BBR cations, four UDCA anions and eighteen $H_2O$ molecules per unit cell. (FIG. 5.)

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound.

The following examples are meant to be illustrative of the practice of the invention, and not limiting in any way.

EXAMPLES

List of Abbreviations

NAFLD: non-alcoholic fatty liver disease
BBR: berberine
UDCA: ursodeoxycholic acid
BUDCA: berberine ursodeoxycholate
LDL-c: low density lipoprotein cholesterol
NASH: non-alcoholic steatohepatitis
PK: pharmacokinetic
PD: pharmacodynamic
TC: total cholesterol
TG: triglyceride

Example 1. A phase 1b Randomized and Controlled Study on Pharmacokinetics and Pharmacodynamics of BUDCA in Patients with Hyperlipidemia A double-blind, randomized, placebo-controlled, dose ranging study was carried out that compared three doses of berberine ursodeoxycholate (BUDCA, a.k.a. HTD1801) to placebo in a cohort of subjects with a history of hypercholesterolemia and serum LDL-c levels above 2.59 mmol/L

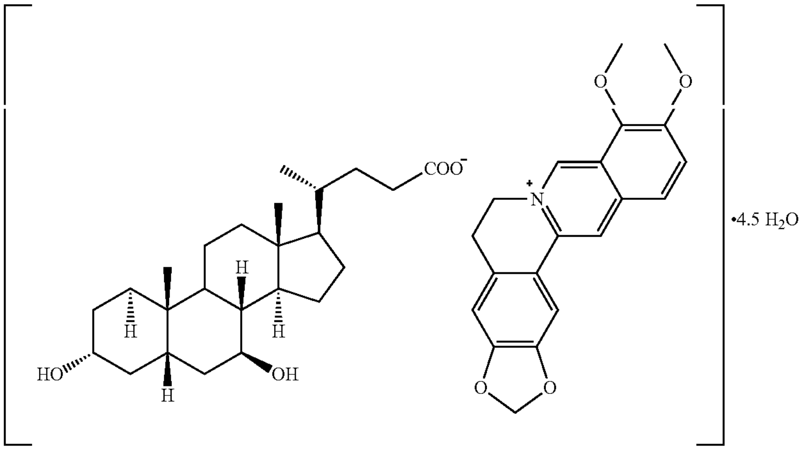

Hemi-nonahydrate of BUDCA (>99.9 mg/dL). BUDCA was administered in two divided doses each day for 28 days. The primary endpoints of the study were safety and tolerability of this new compound, as well as its effect in lowering serum lipid and lipoprotein concentrations.

Methods

Adult subjects were recruited and enrolled into this double-blind, randomized placebo-controlled dose ranging study at one of three research units in Australia between April and December of 2018. The key entry criteria were hypercholesterolemia, with serum LDL-c >2.59 mmol/L (>99.9 mg/dL) and overweight or obesity (BMI between 25 and 40 kg/$m^2$). Subjects were otherwise generally healthy, but were excluded if they had a history of cardiac disease, severe, uncontrolled diabetes or other systemic disorders that might limit their participation in the study. Subjects were asked to discontinue the use of lipid-lowering medications at least 28 days prior to their first dose of BUDCA and for the duration of the study.

Subjects underwent an initial assessment and were then randomized to receive ascending doses of BUDCA in three sequential dosing groups: Group I received 500 mg/day of BUDCA or matching placebo in a ratio of 3:1. Group II received 1,000 mg/day of BUDCA or placebo, 3:1 and Group III received 2,000 mg/day BUDCA or placebo, 3:1. Study medication or placebo was given in two equal doses daily for 28 days. The investigational product BUDCA was administered in the form of film-coated tablets, each tablet containing 250 mg of BUDCA. The placebo was identical in appearance to the active agent. Subjects were instructed to take their tablets after breakfast and after dinner respectively with a glass of water.

The groups were enrolled sequentially, but follow-up overlapped (the next cohort could begin during the follow-up period of the prior cohort) (FIG. 1). The decision to move to the next dose level was based upon tolerability and safety findings, as assessed by a Safety Monitoring Committee. Individual subjects were admitted overnight for their first and last doses and so as to draw blood samples for pharmacokinetic studies; in between, they were seen every few days. Subjects were asked to arrive in a fasting state (typically overnight). After having vital signs measured and baseline laboratory tests taken, the subject was given a morning meal and then observed while taking their first dose of BUDCA with a glass of water. They stayed overnight to allow sampling for PK studies which were drawn at the following time points −18 hours, −12, −6, 0 time (pre-dose), +0.25 (post-dose), +0.5, +1, +2, +3, +4, +8, +12, +24 hours. Blood samples for PK studies were collected in dipotassium ethylene diamine tetra-acetic acid (K2EDTA) as the anticoagulant and the assays were done on plasma.

Blood samples for serum biochemistry (including lipid levels) and blood counts were drawn with subjects in a fasting state, at baseline and every 14 days through the study. Samples were shipped in a refrigerated state to laboratory where testing was done using routine clinical methodology, as follows: HbA1c was measured by ion-exchange HPLC (Bio-Rad D-100). For samples received by the laboratory prior to Sep. 2, 2018, the following analytes were measured on the Roche Diagnostics Modular P100 platform (ALT by photometric assay, TC by Trinder peroxidase assay, LDL-c by photometric assay, HDL-c by homogenous enzymatic colorimetric assay and TG by photometric assay). For samples received by the laboratory after Sep. 2, 2018, the following analytes were measured on the Beckman Coulter AU 5800 platform (ALT by photometric assay, TC by cholesterol-oxidase/peroxidase assay, LDL-c by homogenous enzymatic colorimetric assay, HDL-c by immune inhibition and cholesterol oxidase assay and TG by an enzymatic method using opiase/GK/GPO-PAP-4 amino phenazone).

Subjects received dietary counseling with regard to healthy eating habits and use of study medication at several times points in the study. For the pharmacokinetic profile of BUDCA, serum levels of BBR and UDCA were measured after single and multiple doses. PK sampling was done at multiple intervals before and up to 24 hours after the first dose of study drug on day 1 and again on day 28.

Concentrations of BBR and UDCA in plasma were determined simultaneously by liquid chromatography tandem-mass spectrometry (LC-MS/MS). Although assays for both berberine and UDCA have been commonly used, the challenge for this study was to measure both analytes simultaneously in the same sample; hence the need for further methodology development beyond what has previously been done for berberine and UDCA separately, as these two analytes are quite different.

The study was conducted in accordance with the International Council for Harmonisation tripartite guideline on the ethical principles of Good Clinical Practice (ICHE6). The study was approved by Independent Ethics Committees (IECs) at each of the participating institutions and all subjects gave written informed consent to participate.

Statistical analysis: Data from all cohorts were summarized by treatment group in the order: Placebo, BUDCA 500 mg, BUDCA 1,000 mg, and BUDCA 2,000 mg. Mean changes and percent changes from baseline were computed for lipids, glucose, liver function, hematology, serum chemistry, and urinalysis measures. Percentage measures involving continuous measures were computed for each patient and then averaged while percentage calculations involving rates used the number of subjects as, the denominator was the number of subjects in the relevant population, unless otherwise stated. Pre-planned ANOVA analyses were conducted to perform global comparisons for the separate changes from baseline to Days 14 and 28 across all four treatment groups in order to control Type 1 error for making pre-planned comparisons of each active dose vs. placebo; log transformations were used to normalize the inherent variability in clinical laboratory results; if the ANOVA analyses achieved statistical significance, then two-sided p-values were justified to compare each active dose group vs. the pooled placebo controls using unpaired comparisons from ANOVA output. SAS version 9.3 was used for all analyses.

Results

A total of 50 subjects were enrolled into three dose cohorts in this study. BUDCA was generally well tolerated, even at doses of 2,000 mg per day (the highest dose group); this highest dose was associated with significant reductions in LDL-c. By day 28 and with the highest dose of BUDCA, there were significant reductions in the serum concentrations of TC by 8.2% (P=0.0004) and LDL-c by 10.4% (P=0.0006), but no significant changes in TG and HDL-c concentrations.

Fifty subjects were enrolled, including 30 females, equally distributed across the three dosing groups, 38 receiving BUDCA and 12 receiving placebo. The baseline characteristics of enrolled subjects are shown in Table 1. Their mean LDL-c levels were 3.86 mmol/L (range 2.5 to 5.9). Only three had a history of diabetes or glucose intolerance and Hb1Ac levels were mostly in the normal range.

TABLE 1

Baseline Subject Characteristics and Biochemistry Profile

| Characteristic | Placebo | BUDCA Dose 500 mg/day | 1,000 mg/day | 2,000 mg/day |
|---|---|---|---|---|
| Number of Subjects | 12 | 12 | 12 | 14 |
| Mean age, yrs (range) | 53 (26-63) | 48 (27-70) | 54 (42-63) | 52 (22-70) |
| Gender (% female) | 75% | 50% | 42% | 71% |
| Race (% white) | 92% | 100% | 100% | 100% |
| Mean weight, kg (range) | 88 (68-100) | 95 (71-147) | 88 (70-121) | 84 (63-117) |
| Mean BMI ($kg/m^2$) | 30.9 (26-39) | 31.1 (27-39) | 29.5 (25-35) | 30.3 (25-40) |
| History of diabetes or glucose intolerance | 0 | 0 | 1 | 2 |
| History of Hypertension | 3 | 4 | 2 | 1 |
| Mean TC (mmol/L) | 6.06 (4.6-10.8) | 6.09 (4.4-7.4) | 5.96 (4.6-7.1) | 6.11 (4.5-8.3) |
| Mean LDL-c (mmol/L) | 3.99 (2.7-5.4) | 4.09 (2.8-5.8) | 3.57 (2.7-5.1) | 3.78 (2.5-5.9) |
| Mean TG (mmol/L) | 1.98 (0.6-6.8) | 2.11 (0.6-4.6) | 1.65 (0.4-4.4) | 1.50 (0.7-3.3) |
| Mean HbA1c (%) | 5.3 (4.9-5.7) | 5.4 (4.9-6.0) | 5.2 (5.0-5.5) | 5.6 (5.1-7.4) |
| Mean ALT (U/L) | 20 (12-56) | 26 (7-46) | 24 (13-43) | 20 (12-42) |

TABLE 2

Change in Serum Lipids and Lipoproteins with BUDCA Therapy

| Lipid | Time | Placebo | 500 mg/day | P Value vs. placebo | 1,000 mg/day | ANOVA P Value vs. placebo | 2,000 mg/day | ANOVA P Value vs. placebo |
|---|---|---|---|---|---|---|---|---|
| TG | Baseline* | 1.91 | 2.11 | — | 1.76 | — | 1.60 | — |
| | Day 14 | 1.84 | 1.89 | n.s. | 1.73 | n.s. | 1.42 | n.s. |
| | Day 28 | 2.58 | 2.27 | n.s. | 1.86 | 0.028 | 1.54 | 0.0018 |
| TC | Baseline* | 6.23 | 6.13 | — | 5.81 | — | 5.91 | — |
| | Day 14 | 6.39 | 5.96 | n.s. | 5.51 | n.s. | 5.37 | 0.01 |
| | Day 28 | 6.59 | 5.88 | n.s. | 5.54 | n.s. | 5.42 | 0.003 |
| LDL-c | Baseline* | 3.91 | 4.01 | — | 3.68 | — | 3.85 | — |
| | Day 14 | 4.05 | 3.87 | n.s. | 3.42 | n.s. | 3.40 | 0.0093 |
| | Day 28 | 3.85 | 3.72 | n.s. | 3.51 | n.s. | 3.44 | 0.091 |
| Non-HDL-c | Baseline* | 4.66 | 4.85 | — | 4.48 | — | 4.62 | — |
| | Day 14 | 4.90 | 4.75 | n.s. | 4.23 | n.s. | 4.04 | 0.0018 |
| | Day 28 | 5.18 | 4.71 | 0.03 | 4.31 | 0.025 | 4.14 | 0.0002 |
| HDL-c | Baseline* | 1.55 | 1.25 | — | 1.32 | — | 1.24 | — |
| | Day 14 | 1.49 | 1.22 | n.s. | 1.29 | n.s. | 1.33 | n.s. |
| | Day 28 | 1.42 | 1.17 | n.s. | 1.23 | n.s. | 1.29 | n.s. |

*Baseline value is calculated from mean of Screening and Baseline visits

Figure 2:
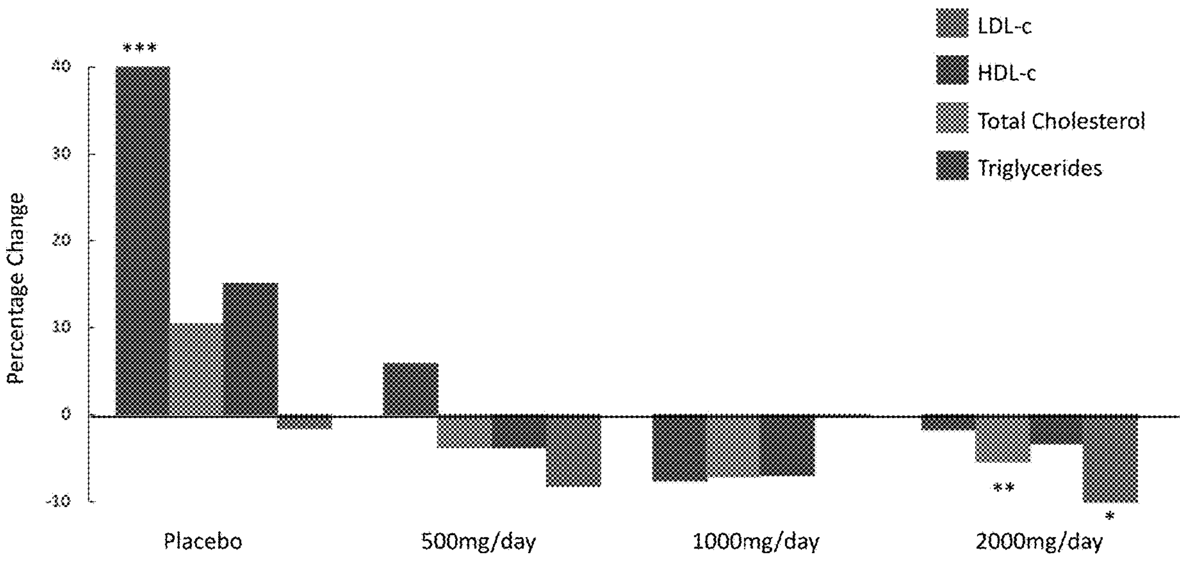
FIG. 2 depicts exemplary percentage change in serum lipids at day 28. Marked parameters were statistically significantly different from baseline (*P=0.0006; P=0.0004; * P=0.0006).

Among the subjects receiving active therapy, serum lipid levels decreased in a dose-dependent fashion (Table 2 and FIG. 2), with maximum reductions relative to placebo being observed after 14 days of treatment, with little further reduction beyond that. HbA1C and ALT levels did not change significantly during therapy. Significant differences were observed between study treatment via ANOVA for TG (Day 28 change from baseline), TC (both Days 14 and change from baseline), LDL-c (both Days 14 and 28 change from baseline), and non-HDL-c (Days 14 and 28 change from baseline). The following pairwise comparisons vs. placebo for the changes from baseline were significant:

TG: Day 28 1,000 mg vs. placebo (P=0.028) and Day 28 2,000 mg vs placebo (p=0.0018)

TC: Days 14 and 28 2000 mg vs. placebo (P=0.01 and 0.003)

LDL-c: Day 14 2,000 mg vs. placebo (P=0.0093)

Non-HDL-c: Days 14 and 28 2000 mg vs. placebo (P=0.0018 and P=0.002), Day 28 1,000 mg vs. placebo (P=0.025) and Day 28 500 mg vs. placebo (P=0.03).

In general, BUDCA was well tolerated and the frequency of adverse events was similar with placebo and active drug, the most frequent complaint in both groups being headache. Three subjects withdrew from the study prior to its completion. The frequency of treatment-related adverse events was similar with placebo (66%) and active drug (67%). Only one subject experienced a serious adverse event, which was thought not to be related to the study drug.

BUDCA has a significant effect in safely lowering serum LDL-c concentrations in individuals with a history of hypercholesterolemia. It may be used for treating hypercholesterolemia in individuals who cannot take statins, and possibly as adjunctive to other agents, such as ezetimibe or bempedoic acid.

Example 2. A Phase 2, Randomized Controlled Trial of BUDCA in Patients with Presumed NASH and Type 2 Diabetes The aim of this study was to determine the effect of two different doses of BUDCA on liver fat content (LFC) in patients with diabetes and presumed NASH when administered for 18 weeks. This phase 2 clinical trial tested the effect of BUDCA in patients with fatty liver disease and diabetes. The group taking the higher dose of this new drug had significant reductions in the amount of fat in their liver as well as improvement in their diabetes.

Methods

A prospective, randomized, placebo-controlled trial of two doses of BUDCA administered orally was conducted in a cohort of 100 subjects with fatty liver disease and diabetes. Treatment was for 18 weeks and endpoints measured included reduction in liver fat content measured by MM proton density fat fraction, improvement in glycemic control, changes in liver-associated enzymes, safety and tolerability.

Patients with diabetes and presumed NASH were randomized into one of three treatment groups, as follows: 1)

BUDCA 500 mg BID 2) 1,000 mg BID and 3) matching placebo. Presumed NASH was defined based largely on magnetic resonance imaging derived proton density fat fraction (MRI-PDFF) of 10% or more. Additional inclusion criteria further enriched the study population for having NASH by virtue of requiring corrected T1 (cT1) of more than 830 milliseconds and elevated serum aspartate aminotransferase (AST)≥20 units per liter (6). Subjects had to be overweight or obese with body mass index of 25 kg/$m^2$ or more.

Study subjects underwent an initial screening evaluation, including measurement of LFC by MRI-PDFF. Subjects were excluded if they had known liver disease other than fatty liver disease or a history of excessive alcohol consumption. Although liver biopsies were not done as a part of this study, subjects with clear evidence of cirrhosis were excluded, based upon a platelet count of less than 150,000/$mm^3$, serum albumin levels less than 3.2 mg/dL or a current or previous history of clinical hepatic decompensation.

Those who were deemed eligible were then randomized into one of the three treatment groups described above and underwent a further baseline evaluation at the time of randomization and initial dosing. Subjects were permitted to continue their current treatment regimen for diabetes provided they had been on a stable dose regimen for at least 90 days.

The treatment duration was for 18 weeks and study subjects were seen at intervals of 2 to 4 weeks throughout. LFC was measured at baseline and after 18 weeks of therapy. In addition, changes in liver chemistry tests, measures of glycemic control and serum lipid levels were also assessed during and at the end of treatment.

The protocol for this study was approved by an institutional review board or ethics committee centrally or at each institution. All subjects gave written, informed consent for their participation.

Statistical methods: Assuming a standard deviation of 6.3% for changes from Baseline in LFC, 35 subjects in each treatment group provided 90% power to show a difference of 5 percentage points between any 2 treatment groups at the 5% level of significance. To allow for a dropout rate of 10%, 39 subjects were randomized to each of the 3 treatment groups.

Descriptive Statistics were used to summarize continuous data, and frequencies and percentages were used to summarize categorical data. The Safety Set consisted of all subjects who received at least one dose of study treatment. The Modified Efficacy Set is a subset of the Safety Set consisting of subjects that had at least one post-dose MRI-PDFF assessment. The Efficacy Set is a subset of the Modified Efficacy Set consisting of subjects that completed at least 80 days of study drug dosing and had a week 18 or Early Termination (ET) visit MRI-PDFF assessment. The primary endpoint was an absolute change from Baseline to Week 18 (or ET) in Liver Fat Content. Primary Endpoint summary measures were provided in both the Efficacy and Modified Efficacy sets, with the Efficacy Set prespecified as the primary analysis set. All other endpoints were prespecified to use the Modified Efficacy Set. Comparisons between active treatment groups relative to placebo were tested using Analysis of Covariance (ANCOVA) with treatment group as a fixed effect and baseline value of the parameters of interest as covariates. ANCOVA based LS Means and raw means have been reported. For statistical analysis of laboratory parameters (i.e. P-values), multiple imputation was used to take missing data into account. A two-sided alpha level of 0.05 without adjustment for multiple tests was used to indicate statistical significance. Analyses were performed using SAS System version 9.4.

Results

Subjects that received 1,000 mg twice a day of BUDCA had significantly greater reduction in liver fat content compared to placebo (mean absolute decrease −4.8% vs. −2.0% [P=0.011], mean relative decrease −24.1 vs −8.3% [P=0.016]). Also, compared to placebo, subjects receiving this dose also experienced significant improvement in glycemic control as well as reductions in serum alanine aminotransferase (ALT) and gamma glutamyl transferase (GGT) activities. Serum lipid levels decreased modestly during therapy. The higher dose of BUDCA was associated with an average weight loss (LS Mean) of −3.5 kg compared to only −1.1 kg with placebo (P=0.012). Diarrhea and abdominal discomfort were the most frequently reported adverse events.

Figure 3:
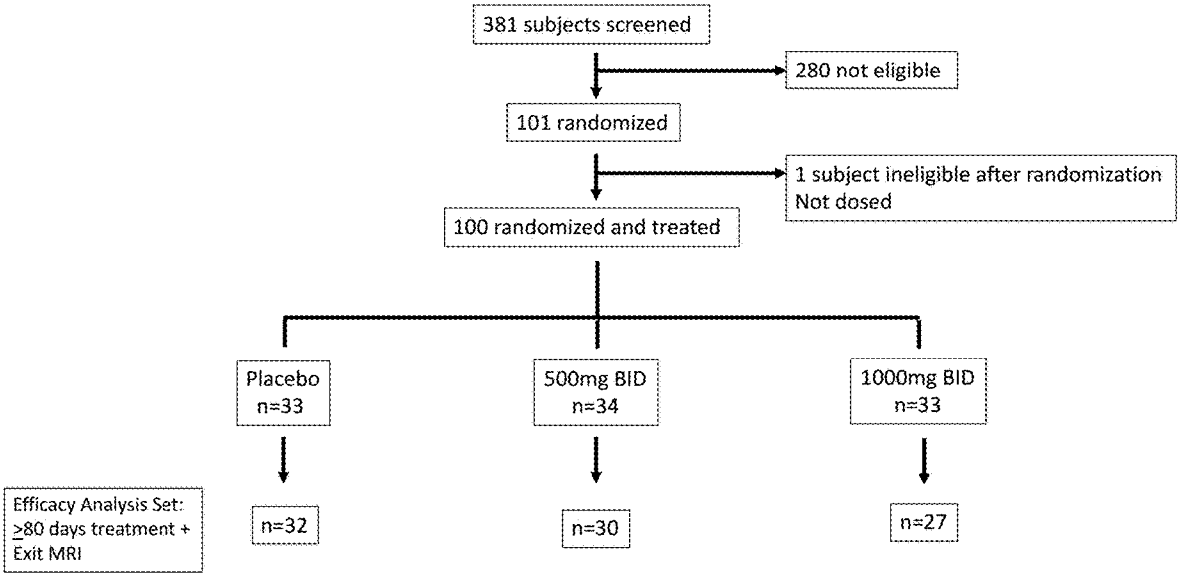
FIG. 3 depicts a CONSORT Diagram for the phase 2 trial.

There were 101 patients enrolled in this study. One did not meet entry criteria and was not dosed (FIG. 3, CONSOR T diagram). Of the remaining 100 subjects, their mean age was 56 years (range 26 to 75) and they included 72 females. Most of the subjects (91%) were white and 38% were of Hispanic ethnicity. Although all patients had a history of diabetes, the mean HbA1c level of those who enrolled was 7.1% (range 5.1 to 9.4%). Of note, 94 of 100 subjects were taking medication(s) for the treatment of their diabetes, often two or more agents at the same time (Table 3A). In addition, many were also taking lipid-lowering therapy as well (Table 3B). Findings from multiparametric Mill showed that the mean liver fat content of the subjects was 19.4% (range 9.0 to 43.5%) and mean corrected T1 was 940 (range 802 to 1412). The demographic and baseline characteristics of the subjects was evenly distributed across the three dosing groups (Table 3A).

TABLE 3A

Baseline Characteristics

| | Treatment Group | | |
|---|---|---|---|
| | Placebo N = 33 | 500 mg BID N = 33 | 1,000 mg BID N = 34 |
| Age (years) | | | |
| N | 33 | 33 | 34 |
| Mean (SD) | 58 (10.7) | 58 (10.2) | 53 (12.2) |
| Min, Max | 40, 75 | 26, 75 | 27, 72 |
| Sex - n (%) | | | |
| Male | 11 (33%) | 7 (21%) | 10 (29%) |
| Female | 22 (67%) | 26 (79%) | 24 (71%) |
| Race - n (%) | | | |
| White | 31 (94%) | 29 (88%) | 31 (91%) |
| Black | 0 | 3 (9%) | 2 (6%) |
| Other | 2 (6%) | 1 (3%) | 1 (3%) |
| Ethnicity - n (%) | | | |
| Hispanic or Latino | 13 (39%) | 14 (42%) | 11 (32%) |
| Not Hispanic or Latino | 20 (61%) | 19 (58%) | 23 (68%) |
| Weight (kg) | | | |
| N | 33 | 33 | 34 |
| Mean (SD) | 97.5 (22.57) | 98.4 (23.05) | 101.2 (20.26) |
| Min, Max | 70.8, 180 | 64.9, 154.1 | 71.7, 159.2 |
| BMI (kg/$m^2$) | | | |
| N | 33 | 33 | 34 |

TABLE 3A-continued

| Baseline Characteristics | Treatment Group | | |
|---|---|---|---|
| | Placebo N = 33 | 500 mg BID N = 33 | 1,000 mg BID N = 34 |
| Mean (SD) | 35.0 (6.18) | 36.7 (6.88) | 36.3 (6.28) |
| Min, Max | 25.4, 55.6 | 26.1, 55.9 | 25.4, 49.1 |
| Liver fat content (%)* | | | |
| N | 32 | 33 | 34 |
| Mean (SD) | 20.2 (6.23) | 18.4 (6.24) | 19.4 (6.96) |
| Min, Max | 11.1, 41.7 | 11.0, 43.48 | 9.0, 33.7 |
| Corrected T1* | | | |
| N | 32 | 32 | 32 |
| Mean (SD) | 940.8 (99.27) | 948.8 (119.53) | 932.4 (80.06) |
| Min, Max | 834.0, 1317.0 | 802.5, 1412.0 | 837.5, 1122.0 |
| ALT (U/L) | | | |
| N | 33 | 33 | 34 |
| Mean (SD) | 54 (26.7) | 46 (27.6) | 62 (31.8) |
| Median | 47 | 39 | 55 |
| Min, Max | 17, 115 | 3, 141 | 24, 143 |
| AST (U/L) | | | |
| N | 33 | 33 | 34 |
| Mean (SD) | 38 (17.3) | 36 (15.9) | 45 (29.7) |
| Median | 32 | 31 | 37 |
| Min, Max | 19, 88 | 15, 80 | 19, 147 |
| GGT (U/L) | | | |
| N | 33 | 33 | 34 |
| Mean (SD) | 70 (105.1) | 64 (50.7) | 68 (57.2) |
| Median | 38 | 39 | 45 |
| Min, Max | 19, 618 | 18, 223 | 19, 263 |
| HbA1c (%) | | | |
| N | 33 | 33 | 34 |
| Mean (SD) | 7.0 (1.05) | 6.9 (0.85) | 7.3 (1.16) |
| Median | 6.9 | 6.9 | 7.5 |
| Min, Max | 5.3, 9.4 | 5.5, 9.1 | 5.1, 9.3 |
| LDL-c(mg/dL)** | | | |
| N | 33 | 30 | 29 |
| Mean (SD) | 99 (35.8) | 86 (29.4) | 107 (35.3) |
| Median | 98 | 81 | 111 |
| Min, Max | 37, 188 | 26, 150 | 31, 168 |
| TG (mg/dL)** | | | |
| N | 33 | 31 | 30 |
| Mean (SD) | 197 (83.3) | 190 (204.6) | 174 (77.1) |
| Min, Max | 76, 423 | 54, 1217 | 58, 430 |
| Fasting insulin (IU/mL) | | | |
| N | 33 | 33 | 34 |
| Mean (SD) | 45.7 (34.64) | 30.8 (15.74) | 32.9 (16.43) |
| Min, Max | 6.2, 155.4 | 9.5, 70.7 | 9.6, 82.4 |
| Fasting plasma glucose (mg/dL) | | | |
| N | 33 | 33 | 34 |
| Mean (SD) | 136 (44.1) | 140 (39.9) | 155 (46.3) |
| Min, Max | 94, 313 | 89, 288 | 90, 268 |

*Multiparametric MRI assessment

**Modified Efficacy Set

TABLE 3B

| Concomitant Medications of Interest at Baseline | | Treatment Group | | |
|---|---|---|---|---|
| | | Placebo N = 33 | 500 mg BID N = 33 | 1,000 mg BID N = 34 |
| For diabetes | Metformin | 28 (85%) | 24 (73%) | 27 (79%) |
| | GLP-1 agonists | 12 (36%) | 6 (18%) | 7 (21%) |
| | Sulfonylureas | 8 (24%) | 5 (15%) | 6 (18%) |
| | Insulin/s | 8 (24%) | 1 (3%) | 7 (21%) |
| | SGLT-2 inhibitors | 3 (10%) | 5 (15%) | 3 (10%) |
| | DPP-4 inhibitors | 3 (10%) | 1 (3%) | 5 (15%) |
| | Fixed dose combinations | 4 (12%) | 2 (6%) | 1 (3%) |
| | Repaglinide | 1 (3%) | 0 | 0 |
| | Pioglitazone | 0 | 1 (3%) | 0 |
| For hyper-lipidemia | HMG CoA Reductase Inhibitors | 15 (45%) | 23 (70%) | 12 (35%) |
| | Fibrates | 2 (6%) | 4 (12%) | 4 (12%) |
| | Fish Oil and Omega-3 Fatty Acids | 9 (27%) | 2 (6%) | 5 (15%) |
| | Colesevalam | 0 | 0 | 1 (3%) |
| | PCSK9 Inhibitors | 1 (3%) | 0 | 0 |
| Other | Vitamin E | 2 (6%) | 0 | 0 |

Table 4A summarizes the changes seen with therapy, according to treatment group. In general, best treatment responses were seen with the higher dose of BUDCA (1,000 mg BID). On average, absolute LFC decreased by 4.8% in this high dose group, compared to only 2.0% with placebo (p=0.011). The relative decrease in LFC in this group was 24.1%, compared to 8.3% with placebo (p=0.016). While there was an apparent dose response with regard to the proportion achieving at least a 5% absolute decrease or a 30% relative decrease in LFC, these changes were not statistically significant. Other biochemical parameters associated with NASH and NAFLD also improved on therapy with this dose, as noted by significant decreases in serum ALT and GGT levels.

TABLE 4A

| Responses to Therapy | Treatment Group | | |
|---|---|---|---|
| | Placebo | 500 mg BID | 1,000 mg BID |
| Absolute Change in LFC (%)* | | | |
| N | 32 | 30 | 27 |
| Mean (SD) | −2.0 (4.88) | −2.9 (4.02) | −4.8 (4.35) |
| Min, Max | −13.9, 6.3 | −11.5, 5.9 | −14.2, 2.9 |
| LS Mean (SE) | −1.8 (0.74) | −3.2 (0.77) | −4.7 (0.81) |
| P-value | | 0.199 | 0.011 |
| Relative Change in LFC (%)* | | | |
| N | 32 | 30 | 27 |
| Mean (SD) | −8.3 (24.48) | −15.1 (22.78) | −24.1 (21.70) |
| Min, Max | −58.3, 46.6 | −66.4, 35.3 | −60.7, 22.1 |
| LS Mean (SE) | −8.2 (4.09) | −15.9 (4.27) | −23.3 (4.53) |
| P-value | | 0.196 | 0.016 |
| Proportion achieving ≥5% Absolute Reduction in LFC*[a] | 8/33 (24%) | 10/31 (32%) | 12/30 (40%) |

TABLE 4A-continued

| Responses to Therapy | | | |
|---|---|---|---|
| | Treatment Group | | |
| | Placebo | 500 mg BID | 1,000 mg BID |
| Proportion achieving ≥30% relative reduction in LFC*[a] | 7/33 (21%) | 6/31 (19%) | 10/30 (33%) |
| Mean change in HbA1c (%)** | | | |
| N | 32 | 29 | 26 |
| Mean (SD) | 0.1 (0.82) | −0.3 (0.68) | −0.6 (0.96) |
| Min, Max | −1.4, 2.7 | −1.8, 1.3 | −2.9, 1.6 |
| LS Mean (SE) | 0.1 (0.14) | −0.4 (0.15) | −0.5 (0.16) |
| P-value | | 0.029 | 0.005 |
| Mean change in ALT (U/L)** | | | |
| N | 32 | 29 | 26 |
| Mean (SD) | −3 (19.2) | −4 (17.9) | −19 (27.2) |
| Min, Max | −50, 47 | −33, 52 | −89, 18 |
| LS Mean (SE) | −2 (3.5) | −5 (3.7) | −16 (3.8) |
| P-value | | 0.674 | 0.007 |
| Relative change in ALT (%)** | | | |
| N | 32 | 29 | 26 |
| Mean (SD) | −6 (30.5) | −6 (36.0) | −21 (35.2) |
| Min, Max | −52, 69 | −60, 89 | −83, 45 |
| Mean change in GGT (U/L)** | | | |
| N | 32 | 29 | 26 |
| Mean (SD) | −2 (34.9) | −19 (26.4) | −30 (47.9) |
| Min, Max | −120, 124 | −104, 21 | −213, 18 |
| LS Mean (SE) | −1 (4.6) | −20 (4.8) | −25 (5.0) |
| P-value | | 0.005 | <0.001 |
| Relative change in GGT (%)** | | | |
| N | 32 | 29 | 26 |
| Mean (SD) | 5 (39.7) | −23 (25.8) | −29 (27.1) |
| Min, Max | −46, 175 | −62, 64 | −81, 24 |
| Mean change in LDL-c (mg/dL)** | | | |
| N | 29 | 27 | 25 |
| Mean (SD) | 0 (20.5) | 5 (34.1) | −16 (26.5) |
| Min, Max | −54, 48 | −33, 147 | −103, 31 |
| LS Mean (SE) | 1 (5.3) | 1 (5.4) | −12 (5.5) |
| P-value | | 0.955 | 0.072 |
| Mean change in TG (mg/dL)** | | | |
| N | 32 | 29 | 26 |
| Mean (SD) | 18 (142.9) | −41 (136.3) | −24 (70.4) |
| Min, Max | −242, 632 | −710, 98 | −161, 154 |
| LS Mean (SE) | 19 (18.5) | −36 (19.4) | −24 (20.4) |
| P-value | | 0.041 | 0.120 |
| Mean change in Body weight (kg)*** | | | |
| N | 32 | 29 | 27 |
| Mean (SD) | −1.1 (2.86) | −1.6 (3.02) | −3.5 (4.77) |
| Min, Max | −9.1, 3.8 | −7.2, 5.9 | −18.9, 4.5 |
| LS Mean (SE) | −1.1 (0.64) | −1.6 (0.67) | −3.5 (0.70) |
| P-value | | 0.554 | 0.012 |

*Primary Endpoint results for Efficacy Set

[a]A Placebo subject had data available at Week 18/ET but did not have baseline data, so they were not included in the absolute and relative change from baseline analyses in the Efficacy Set.

**Modified Efficacy Set

***Safety Set

Note:

P-values and LS Means are obtained from an ANCOVA model with treatment group as a fixed effect, and Baseline value of associated parameters as covariates.

TABLE 4B

| Change in Bile Acids from Baseline to Week 18 in 1000 mg treatment group | | |
|---|---|---|
| | Absolute Change from Baseline | Percent Change from Baseline |
| Total bile acids | | |
| Mean (SD) | 1625 (2332.2) | 256 (455.8) |
| Min, Max | −3075, 6179 | −46, 1437 |
| 1000 mg vs Placebo ANCOVA P-value | 0.016 | |
| Primary bile acids and metabolites | | |
| Mean (SD) | −171 (883.1) | 114 (371.3) |
| Min, Max | −1495, 1484 | −71, 1118 |
| 1000 mg vs Placebo ANCOVA P-value | 0.882 | |
| Secondary bile acids and metabolites | | |
| Mean (SD) | −28 (300.6) | −13 (83.6) |
| Min, Max | −486, 667 | −100, 167 |
| 1000 mg vs Placebo ANCOVA P-value | 0.459 | |
| Urso bile acids | | |
| Mean (SD) | 1824 (2122.6) | 4741 (7699.7) |
| Median | 2072 | 1975 |
| Min, Max | −2787, 4964 | −80, 27623 |
| 1000 mg vs Placebo ANCOVA P-value | <0.001 | |

Note:

p-values are obtained from an ANCOVA model with treatment group as a fixed effect, and Baseline value of the given laboratory assessment as a covariate.

Notably, significant improvements were also seen in glycemic control with BUDCA therapy. Mean HbA1c levels decreased by 0.6% in the 1,000 mg BID group and 0.3% in the 500 mg BID group compared to an increase of 0.1% in the placebo group. No significant changes were noted in levels of blood glucose, insulin or HOMA-IR.

Figure 4:
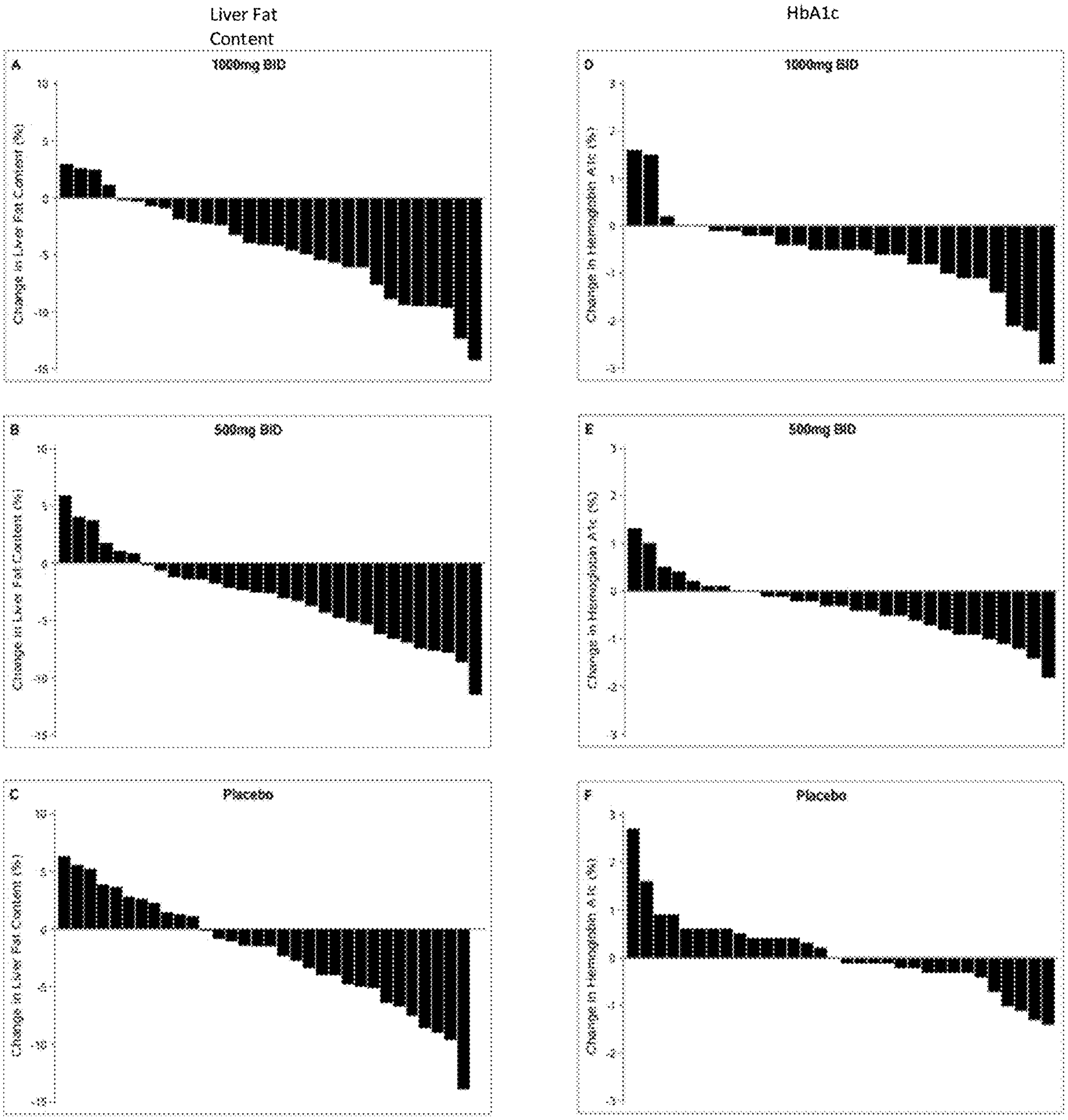
FIG. 4 depicts an exemplary waterfall plot of change in LFC and HbA1C among subjects receiving BUDCA 1,000 mg BID vs Placebo

Favorable decreases were also noted in plasma lipid and lipoprotein levels. Levels of LDL-c decreased by an average of 16 mg/dL in the high dose group (P=0.072) and triglyceride levels decreased by 41 mg/dL in the 500 mg BID dose group (P=0.04), although not with the higher dose. There was no significant change in levels of HDL-c. Finally, subjects receiving the higher dose lost an average of 3.5 kg in weight (P=0.012). FIG. 4 shows the decreases in liver fat content, HbA1c and body weight in individual subjects.

Changes in serum levels of bile acids were noted (Table 4B) and were consistent with changes expected to occur with UDCA therapy. Table 3A shows these changes from baseline in the highest dose group (1,000 mg BID). While there was an increase in the total bile acids, levels of primary and secondary bile acids and their metabolites decreased, but a dramatic increase was noted in the levels of urso-bile acid and their metabolites.

Effects of treatment with BUDCA on AST to Platelet Ratio Index (APRI) and Fibrosis-4 (FIB-4) were also measured.

Figure 6:
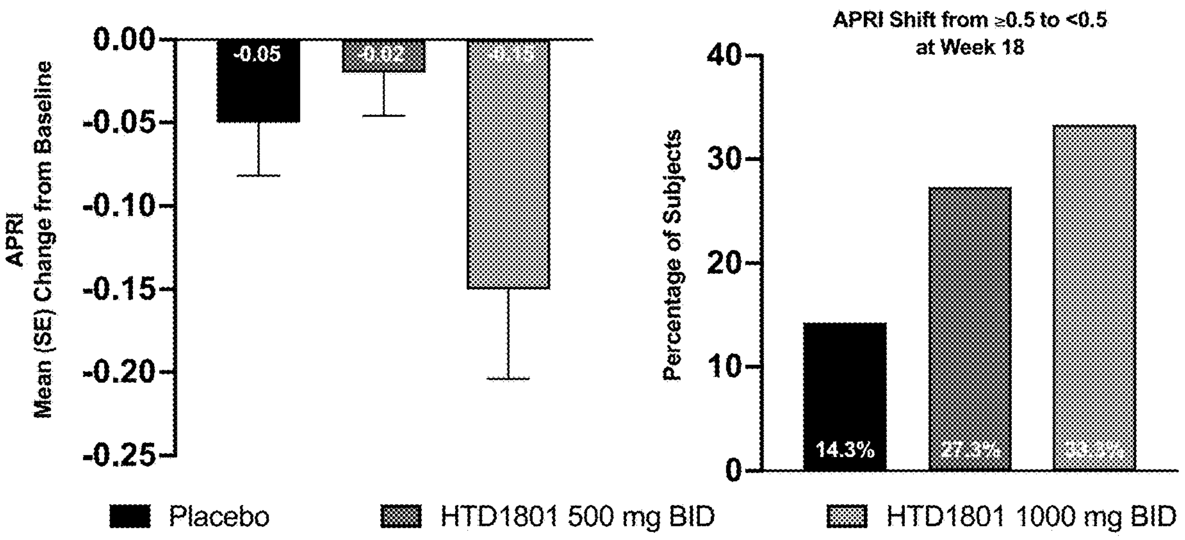
FIG. 6 depicts exemplary data showing an approximately 3-fold greater reduction in APRI with 1000 mg BUDCA vs Placebo after 18 weeks.

An approximately 3-fold greater reduction in APRI with 1,000 mg BUDCA vs placebo after 18 weeks (FIG. 6). Treatment with 1,000 mg BUDCA had approximately 2-fold greater proportion of subjects vs placebo showing improvements in APRI to thresholds associated with less severe fibrosis.

Figure 7:
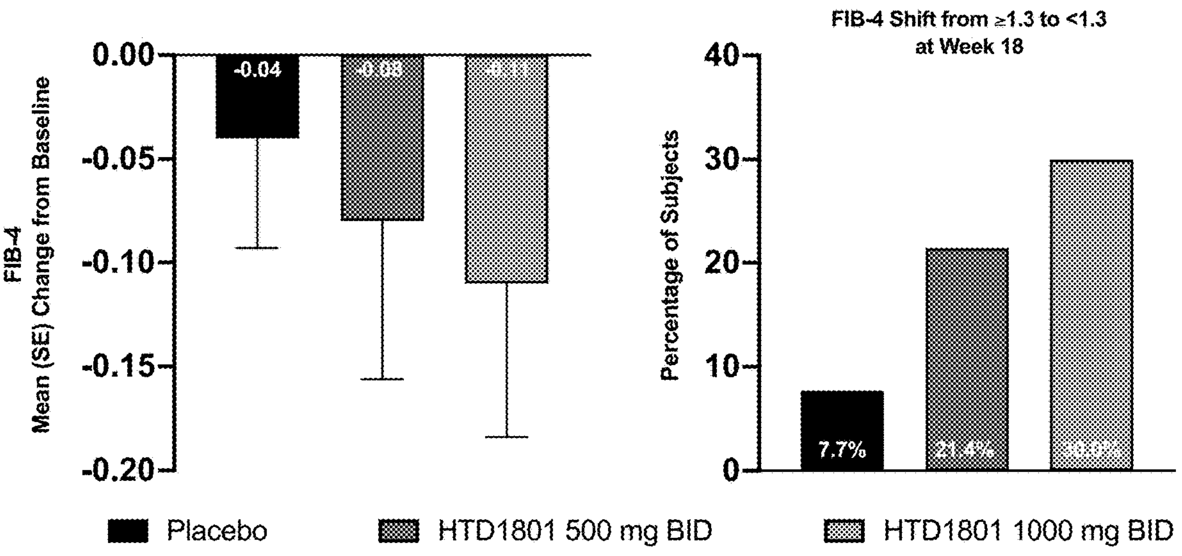
FIG. 7 depicts exemplary data showing an approximately 3-fold greater reduction in FIB-4 with BUDCA 1000 mg vs Placebo after 18 weeks.

Also observed was an approximately 3-fold greater reduction in FIB-4 with BUDCA 1000 mg vs placebo after 18 weeks (FIG. 7). Treatment with 1000 mg BUCDA vs Placebo had approximately 4-fold greater proportion of subjects showing improvements in FIB-4 to thresholds associated with less severe fibrosis.

Figure 8:
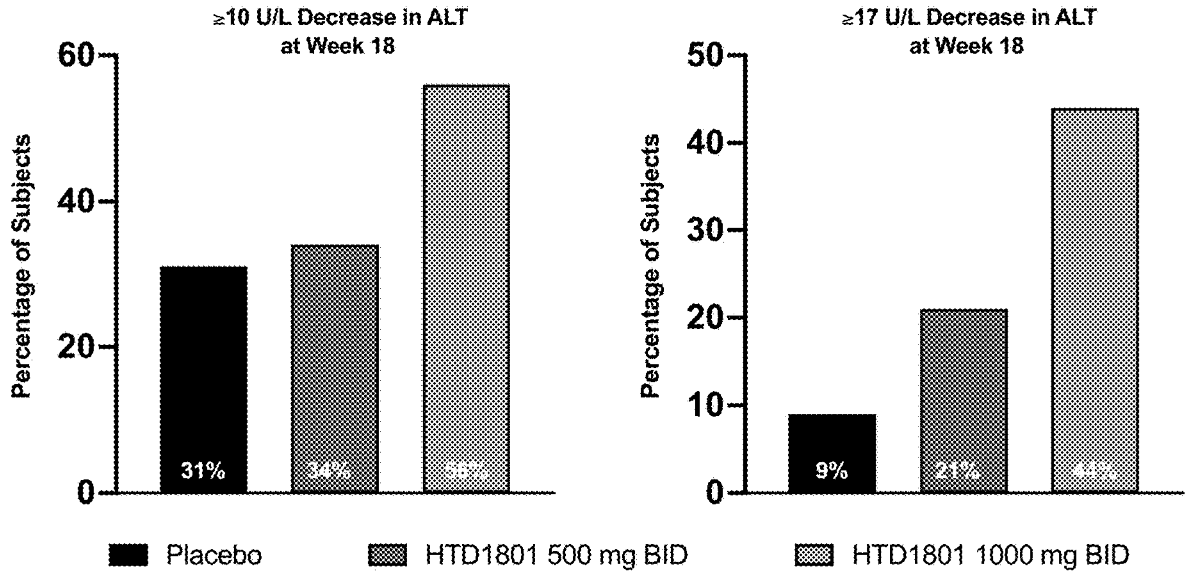
FIG. 8 depicts exemplary data showing a greater percentage of subjects treated with BUDCA achieved better ALT reductions compared to those treated with placebo.

A greater percentage of subjects treated with HTD1801 vs placebo achieved at different ALT reduction changes (FIG. 8) A greater percentage of subjects treated with HTD1801 vs placebo achieved ALT reductions which may be accompanied by potential histological improvement.

No significant differences were observed between enhanced liver fibrosis (ELF) score or Pro-C3 when treated with BUDCA vs placebo (FIG. 9).

BUDCA therapy was generally well tolerated. Table 5 shows that the most frequent adverse event occurring during therapy was diarrhea while some subjects reported symptoms of gastrointestinal reflux or nausea. A similar number of subjects receiving either placebo or BUDCA reported having headaches. These adverse events were generally mild (grade 1 or 2, using CTCAE criteria). None of the serious adverse events occurred during the conduct of this study were attributed to the study drug.

TABLE 5

Adverse Events

| | | Treatment Group | | |
|---|---|---|---|---|
| | | Placebo N = 33 | 500 mg BID N = 33 | 1,000 mg BID N = 34 |
| Subjects with TEAEs Related to Study Drug reported in two or more subjects in any treatment group | Diarrhea | 0 | 4 (12%) | 9 (26%) |
| | GERD | 0 | 2 (6%) | 0 |
| | Nausea | 0 | 1 (3%) | 5 (15%) |
| | Headache | 1 (3%) | 2 (6%) | 1 (3%) |
| Subjects with TEAEs requiring discontinuation of study drug | Diarrhea | 0 | 0 | 2 (6%) |
| | GERD | 0 | 1 (3%) | 1 (3%) |
| | Abdominal distension | 0 | 0 | 1 (3%) |
| | Melena | 0 | 0 | 1 (3%) |
| | Acute myocardial infarction | 0 | 0 | 1 (3%) |
| | Bladder Cancer | 1 (3%) | 0 | 0 |
| | Headache and Facial Rash | 0 | 0 | 2 (6%) |

Two doses of BUDCA were tested in this study. While a dose-dependent effect was noted with some parameters, in general the 500 mg BID dose was less effective than the 1,000 mg BID dose. The adverse event profile was minimal and dose dependent and the drug was generally well tolerated. Results from this phase 2, randomized, placebo-controlled trial show that BUDCA is very effective in decreasing LFC in patients with presumed NASH and diabetes, as assessed by MRI-PDFF. Furthermore, BUDCA is also effective in improving glycemic control, measured by reductions in blood levels of HbA1c. In addition to these key benefits, improvements were seen in levels of liver-associated enzymes (ALT and GGT) as well as lipid levels (LDL-c and TG).

The use of non-invasive tests such as MRI is now well established in early trials of novel agents to treat NASH. Although liver biopsy was not a part of this study, the inclusion criteria allowed for an enrichment of the study population for NASH. All subjects had to have at least 10% LFC by MRI-PDFF and in addition they had to have corrected T1 values on MRI at baseline of at least 830 msec. Furthermore, subjects were all diabetic and were required to have serum AST values of at least 20 U/L—both of these are risk factors for NASH among individuals known to have NAFLD.

Each of the two parent compounds of BUDCA (BBR cation and UDCA anion) are likely to have contributed to the beneficial effects seen in this patient population. Both BBR and UDCA appear to have anti-inflammatory effects, consistent with the reductions seen in serum levels of ALT and GGT although these liver enzymes may have decreased simply because of the decrease in liver fat.

The complex tertiary structure of the BUDCA salt appears to increase the bioavailability of BBR, both locally in the GI tract and systemically, perhaps accounting for the potent effect on glycemic control (data on file).

This study found that the use of BUDCA is also associated with significant body weight loss (an average of 3.5 kg in the group dosed with 1,000 mg BID).

BUDCA was relatively well tolerated. The one serious adverse event occurring in the BUDCA high dose group was not related to the study drug.

The use of BUDCA is associated not only with improvement in features of NASH (LFC, ALT, GGT, APRI and FIB-4) but also in other metabolic parameters including Hb1Ac and serum lipid levels. In contrast, some other agents being tested as treatment for NASH may increase serum levels of cholesterol, often requiring concomitant therapy with an HMG CoA Reductase inhibitor (a "statin") (e.g., obeticholic acid). Other agents (such as pioglitazone) may contribute to weight gain, whereas BUDCA is associated with weight loss. Finally, it should be noted that BUDCA is orally administered whereas some other new agents require regular subcutaneous injection or even intravenous infusion.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

Incorporation by Reference

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Equivalents

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The above examples contain important additional information, exemplification and guidance that can be adapted to the practice of this invention in its various embodiments and equivalents thereof.

What is claimed is:

1. A method for treating hyperlipidemia, comprising administering to a subject in need thereof a therapeutically effective amount of a pharmaceutical composition comprising Berberine Ursodeoxycholate (BUDCA), wherein the subject additionally suffers from diabetes, and wherein the subject is administered from about 500 mg/day to about 5,000 mg/day of BUDCA.

2. A method for reducing low-density lipoprotein cholesterol (LDL-c), total cholesterol (TC), and/or triglyceride (TG) comprising administering to a subject in need thereof a therapeutically effective amount of a pharmaceutical composition comprising BUDCA, wherein the subject additionally suffers from diabetes, and wherein the subject is administered from about 500 mg/day to about 5,000 mg/day of BUDCA.

3. The method of claim 2, for reducing LDL-c, total cholesterol (TC), and triglyceride (TG).

4. The method of claim 2, wherein the subject is administered from about 500 mg to about 1,500 mg BID of BUDCA.

5. The method of claim 4, wherein BUDCA is in the form of Form A.

6. The method of claim 4, wherein BUDCA is a hydrate.

7. The method of claim 4, wherein the subject is also administered one or more of metformin, insulin and a GLP-1 agonist.

8. A method for reducing or slowing the progression of liver fibrosis associated with fatty liver and diabetic diseases, comprising administering to a subject suffering from both fatty liver and diabetic diseases a therapeutically effective amount of a pharmaceutical composition comprising BUDCA, wherein the subject is administered from about 500 mg/day to about 5,000 mg/day of BUDCA, and wherein at least one of AST to Platelet Ratio Index (APRI) and Fibrosis-4 (FIB-4) of the subject is reduced by at least about three-fold.

9. The method of claim 8, wherein the subject suffers from type 2 diabetes.

10. The method of claim 9, wherein the subject is administered from about 500 mg to about 1,500 mg BID of BUDCA.

11. The method of claim 10, wherein both APRI and FIB-4 of the subject are reduced by at least about three-fold.

12. The method of claim 10, wherein BUDCA is in the form of Form A.

13. The method of claim 10, wherein BUDCA is a hydrate.

14. The method of claim 10, wherein administration of BUDCA also simultaneously reduces at least one of low-density lipoprotein cholesterol (LDL-c), total cholesterol (TC), triglyceride (TG), alanine aminotransferase (ALT), gamma glutamyl transferase (GGT), liver fact content (LFC), and body weight.

15. The method of claim 14, wherein the subject simultaneously exhibits liver functional or histologic improvement.

16. The method of claim 15, wherein administration of BUDCA lasts at least 9 weeks.

17. The method of claim 16, wherein the treatment results in a body weight loss of at least 2.0 kg in the subject.

* * * * *